(12) United States Patent
Naicker et al.

(10) Patent No.: US 6,503,921 B2
(45) Date of Patent: *Jan. 7, 2003

(54) DEUTERATED RAPAMYCIN COMPOUNDS, METHODS AND USES THEREOF

(75) Inventors: Selvaraj Naicker, Edmonton (CA); Randall W. Yatscoff, Edmonton (CA); Robert T. Foster, Edmonton (CA)

(73) Assignee: Isotechnika, Inc., Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/987,812

(22) Filed: Nov. 16, 2001

(65) Prior Publication Data

US 2002/0028827 A1 Mar. 7, 2002

Related U.S. Application Data

(63) Continuation of application No. 09/348,015, filed on Jul. 6, 1999, which is a continuation-in-part of application No. 09/148,623, filed on Sep. 4, 1998, now abandoned.
(60) Provisional application No. 60/057,632, filed on Sep. 5, 1997.

(51) Int. Cl.$^7$ .................... C07D 491/16; A61K 31/445
(52) U.S. Cl. ........................................ 514/291; 540/456
(58) Field of Search ........................... 540/456; 514/291

(56) References Cited

PUBLICATIONS

Dennis P. Curran, et al., Intramolecular Hydrogen Transfer Reaction of o–(Bromophenyl)dialklsilyl Ethers. Preparation of Rapamycin–$d_1$, Tetrahedron Letters, vol. 33, No. 17, pp. 2295–2298.

Don Sticker, Senior Technical Information Specialist of Chemical Abstract Service, C.A.S., Commericial Database Search of Deuterated Rapamycin, search conducted Mar. 9, 2000.

Park et al., *Jr. Bio Chem.*, vol. 267, No. 5 (15) pp 3316–3324, 1992.

Connelly et al, *Biochemistry*, vol. 32, pp 5583–5590 (1993).

*Primary Examiner*—Bruck Kifle
(74) *Attorney, Agent, or Firm*—Burns Doane Swecker & Mathis LLP

(57) ABSTRACT

The synthesis of deuterated analogues of rapamycin is disclosed together with a method for use for inducing immunosupression and in the treatment of transplantation rejection, graft vs host disease, autoimmune diseases, diseases of inflammation leukemia/lymphoma, solid tumors, fungal infections, hyperproliferative vascular disorders. Also described is a method for the synthesis of water soluble deuteratred rapamycin compounds and their use as described above.

21 Claims, 2 Drawing Sheets

DEUTERATED RAPAMYCIN COMPOUNDS, METHODS AND USES THEREOF

REFERENCE TO RELATED APPLICATIONS

This application is a continuation of Ser. No. 09/348,015 filed Jul. 6, 1999 which is a continuation-in-part of U.S. patent application Ser. No. 09/148,623, filed Sep. 4, 1998, now abandoned which is based on provisional patent application No. 60/057,632, filed Sep. 5, 1997 both of which are relied on and incorporated herein by reference.

BACKGROUND OF THE INVENTION

This invention relates to deuterated derivatives of rapamycin and a method for using them in the treatment of transplantation rejection, host vs. graft disease, graft vs. host disease, leukemia/lymphoma, hyperproliferative vascular disorders, autoimmune diseases, diseases of inflammation, solid tumors, and fungal infections.

Rapamycin, known as sirolimusis, is a 31-membered macrolide lactone, $C_{51}H_{79}NO_{13}$, with a molecular mass of 913.6 Da. In solution, sirolimus forms two conformational trans-, cis-isomers with a ratio of 4:1 (chloroform) due to hindered rotation around the pipecolic acid amide bond. It is sparingly soluble in water, aliphatic hydrocarbons and diethyl ether, whereas it is soluble in alcohols, halogenated hydrocarbons and dimethyl sulfoxide. Rapamycin is unstable in solution and degrades in plasma and low-, and neutral-pH buffers at 37° C. with half-life of <10 h. the structures of the degradation products have recently been characterized. Rapamycin is a macrocyclic triene antibiotic produced by *Streptomyces hygroscopicus,* which was found to have antifungal activity, particularly against *Candida albicans,* both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)]. Although it shares structural homology with the immunosuppressant tacrolimus and binds to the same intracellular binding protein in lymphocytes, rapamycin inhibits S6p70-kinase and therefore has a mechanism of immunosuppressive action distinct from that of tacrolimus. Rapamycin was found to prolong graft survival of different transplants in several species alone or in combination with other immunosupressants. In animal models its spectrum of toxic effects is different from that of cyclosporin or FK-506., comprising impairment of glucose homeostasis, stomach, ulceration, weight loss and thrombocytopenia, although no nephrotoxicity has been detected.

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. Carboxylic acid esters (PCT application No. WO 92/05179), carbamates (U.S. Pat. No. 5,118,678), amide esters (U.S. Pat. No. 5,118,678), (U.S. Pat. No. 5,118,678) fluorinated esters (U.S. Pat. No. 5,100,883), acetals (U.S. Pat. No. 5,151,413), silyl ethers (U.S. Pat. No. 5,120,842), bicyclic derivatives (U.S. Pat. No. 5,120,725), rapamycin dimers (U.S. Pat. No. 5,120,727) and O-aryl, O-alkyl, O-alkyenyl and O-alkynyl derivatives (U.S. Pat. No. 5,258,389) have been described.

Rapamycin is metabolized by cytochrome P-450 3A to at least six metabolites. During incubation with human liver and small intestinal microsomes, sirolimus was hydroxylated and demethylated and the structure of 39-O-demethyl sirolimus was identified. In bile of sirolimus-treated rats >16 hydroxylated and demethylated metabolites were detected.

In rapamycin, demethylation of methoxy group at C-7 Carbon will lead to the change in the conformation of the Rapamycin due to the interaction of the released C-7 hydroxyl group with the neighbouring pyran ring system which is in equilibrium with the open form of the ring system. The C-7 hydroxyl group will also interact with the triene system and possibly alter the immunosupressive activity of rapamycin. This accounts for the degradation of rapamycin molecule and its altered activity.

Stable isotopes (e.g., deuterium, $^{13}C$, $^{15}N$, $^{18}O$) are non-radioactive isotopes which contain one additional neutron than the normally abundant isotope of the atom in question. Deuterated compounds have been used in pharmaceutical research to investigate the in vivo metabolic fate of the compounds by evaluation of the mechanism of action and metabolic pathway of the non deuterated parent compound. (Blake et al. J. Pharm. Sci. 64, 3, 367–391, 1975). Such metabolic studies are important in the design of safe, effective therapeutic drugs, either because the in vivo active compound administered to the patient or because the metabolites produced from the parent compound prove to be toxic or carcinogenic (Foster et al., Advances in drug Research Vol. 14, pp. 2–36, Academic press, London, 1985).

Incorporation of a heavy atom particularly substitution of deuterium for hydrogen, can give rise to an isotope effect that can alter the pharmacokinetics of the drug. This effect is usually insignificant if the label is placed in a molecule at the metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to kinetic isotope effect. A reaction involving breaking a C—D bond can be up to 700 per cent slower than a similar reaction involving breaking a C—H bond.

More caution has to be observed when using deuterium labeled drugs. If the C—D bond is not involved in any of the steps leading to the metabolite, there may not be any effect to alter the behavior of the drug. If a deuterium is placed at a site involved in the metabolism of a drug, an isotope effect will be observed only if breaking of the C—D bond is the rate limiting step. There are evidences to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway by a process called "metabolic switching".

It is also observed that one of the most important metabolic pathways of compounds containing aromatic systems is hydroxylation leading to a phenolic group in the 3 or 4 position to carbon substituents. Although this pathway involves cleavage of the C—H bond, it is often not accompanied by an isotope effect, because the cleavage of this bond is mostly not involved in the rate-limiting step. The substitution of hydrogen by deuterium at the stereo center will induce a greater effect on the activity of the drug.

Clinically relevant questions include the toxicity of the drug and its metabolite derivatives, the changes in distribution or elimination (enzyme induction), lipophilicity which will have an effect on absorption of the drug. Replacement of hydrogen by deuterium at the site involving the metabolic reaction will lead to increased toxicity of the drug. Replacement of hydrogen by deuterium at the aliphatic carbons will have an isotopic effect to a larger extent. Deuterium placed at an aromatic carbon atom, which will be the site of hydroxylation, may lead to an observable isotope effect, although this is less often the case than with aliphatic carbons. But in few cases such as in penicillin, the substitution on the aromatic ring will induce the restriction of rotation of the ring around the C—C bond leading to a favorable stereo-specific situation to enhance the activity of the drug.

Approaching half a century of stable-isotope usage in human metabolic studies has been without documented significant adverse effect. Side-effects with acute D dosing are transitory with no demonstrated evidence of permanent deleterious action. The threshold of D toxicity has been defined in animals and is far in excess of concentrations conceivably used in human studies (Jones PJ, Leatherdale ST Clin Sci (Colch) April 1991; 80(4):277–280). The possibility that D may have additional beneficial pharmacological applications cannot be excluded. For isotopes other than D, evidence of observed toxicity remains to be produced even at dosages far in excess of the range used in metabolic studies. Absence of adverse effect may be attributable to small mass differences and the similar properties of tracer and predominantly abundant isotopes. The precision of extrapolating toxicity thresholds from animal studies remains unknown. However, should perturbation of the delicate homoeostatic characteristic of living organisms occur with use of stable isotopes, it is almost undoubtedly at some level of administration greatly in excess of those administered currently in biomedical research.

In the prior art, no details are described regarding deuterated derivatives to improve the stability of rapamycin molecule and also about glycosylated deuterated rapamycin to improve the stability and also the solubility of the molecule in order to increase the bio-availability of the drug. We therefore defined the global objective of preparing a rapamycin derivative which is more stable, less prone to degradation, and more water soluble to improve the bio-availability.

SUMMARY OF THE INVENTION

Deuteration of the rapamycin molecule results in altered physicochemical and pharmacokinetic properties which enhance its usefulness in the treatment of transplantation rejection, host vs. graft disease, graft vs. host disease, leukemia/lymphoma, hyperproliferative vascular disorders, autoimmune diseases, diseases of inflammation, solid tumors, and fungal infections.

Deuterium isotope is selected based on the fact that if $^{13}C$, $^{15}N$ or another heavy isotope differing from the light one by less than 10% in mass is incorporated at the site of metabolism, there may be a small isotope effect. In addition to this, there are secondary isotope effects away from the site of isotope substitution due to changes in electronic environment.

Substitution of deuterium in methyl groups of rapamycin will result in a slower rate of oxidation of the C—D bond relative to the rate of oxidation of a non deuterium substituted C—H bond. The isotopic effect acts to reduce formation of demethylated metabolites and thereby alters the pharmacokinetic parameters of the drug. Lower rates of oxidation, metabolism and clearance result in greater and more sustained biological activity. Deuteration is targeted at various sites of the rapamycin molecule to increase the potency of drug, reduce toxicity of the drug, reduce the clearance of the pharmacologically active moiety and improve the stability of the molecule.

DETAILED DESCRIPTION OF THE INVENTION

Figure 1:
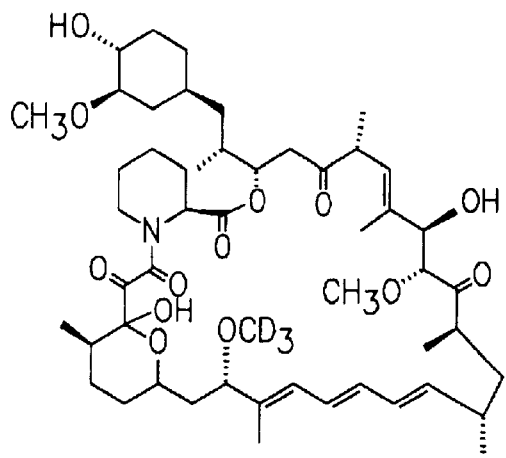
FIG. 1 is the chemical structure of 7-deuteromethyl rapamycin showing sites of deuteration.
Figure 2:
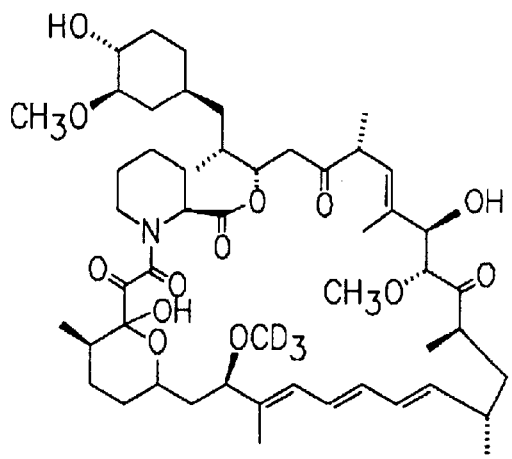
FIG. 2 is the chemical structure of epi-7 deuteromethyl rapamycin showing sites of deuteration.

Substitution of deuterium for ordinary hydrogen and deuterated substrates for protio metabolites can produce profound changes in biosystems. Isotopically altered drugs have shown widely divergent pharmacological effects. Pettersen et al., found increased anti-cancer effect with deuterated 5,6-benzylidene-dl-L-ascorbic acid (Zilascorb) [Anticancer Res. 12, 33 (1992)].

Substitution of deuterium in methyl groups of rapamycin will result in a slower rate of oxidation of the C—D bond relative to the rate of oxidation of a non deuterium substituted C—H bond. The isotopic effect acts to reduce formation of demethylated metabolites and thereby alters the pharmacokinetic parameters of the drug. Lower rates of oxidation, metabolism and clearance result in greater and more sustained biological activity. Deuteration is targeted at various sites of the rapamycin molecule to increase the potency of drug, reduce toxicity of the drug, reduce the clearance of the pharmacologically active moiety and improve the stability of the molecule.

Determination of the physicochemical, toxicological and pharmacokinetic properties can be made using standard chemical and biological assays and through the use of mathematical modeling techniques which are known in the chemical and pharmacological/toxicological arts. The therapeutic utility and dosing regimen can be extrapolated from the results of such techniques and through the use of appropriate pharmacokinetic and/or pharmacodynamic models.

The compounds of this invention may be administered neat or with a pharmaceutical carrier to an animal, such as a warm blooded mammal, and especially humans, in need thereof. The pharmaceutically effective carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, possibly sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The pharmaceutical composition can be in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles administered to a fungally affected area.

EXAMPLES

Figure 5:
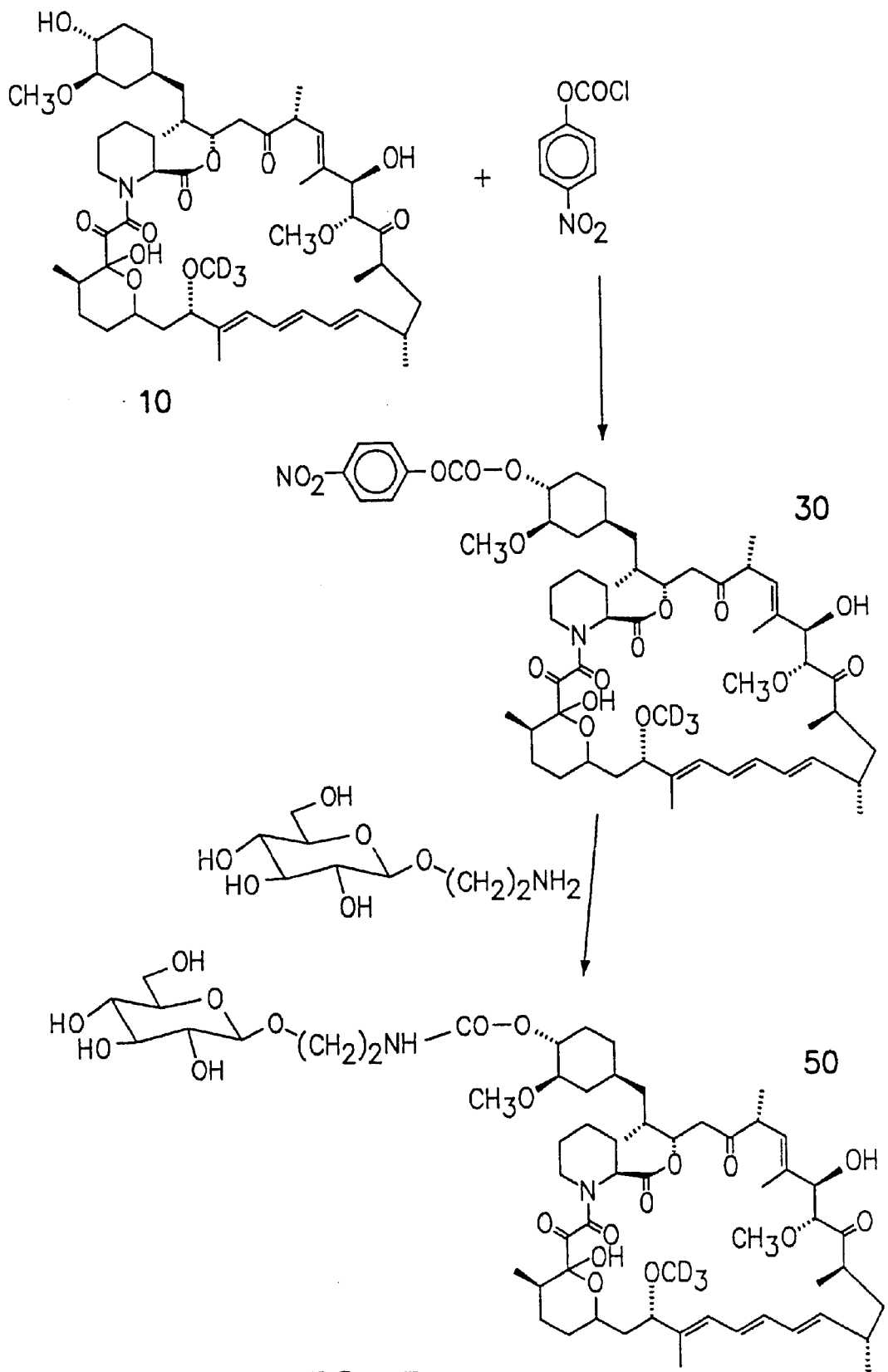
FIG. 5 illustrates the preparation of glycosylated deuterorapamycin.

FIGS. 1–4 show examples of sites for deuteration of the rapamycin molecule. Nonlimiting examples of deuterated rapamycin molecules include the compounds; 7-deuteromethyl rapamycin (FIG. 1), epi-7-deuteromethyl rapamycin (FIG. 2), 7,43-$d_6$-rapamycin (FIG. 3) and 31,42-$d_2$-rapamycin (FIG. 4) including the cis and trans isomers of the compounds shown in FIGS. 1–4. FIG. 5 shows the preparation and structure of the compound glycosylated deuterorapamycin.

Example 1

Preparation of 7-Deuteromethyl Rapamycin (FIG. 1)

5 mg of Rapamycin was dissolved in 2.5 ml of dichloromethane. 40 mg of deuterated methanol was added. 10 beads of NAFION® catalyst were added to the above solution. The contents were stirred under nitrogen at room temperature for 14 hours. The reaction was monitored by mass spectrum. The solution was filtered and concentrated. The residue was dissolved in dry benzene and freeze dried. The white solid obtained was homogenous by mass spectrum analysis and characterized by LC/MS.

Example 2

Figure 3:
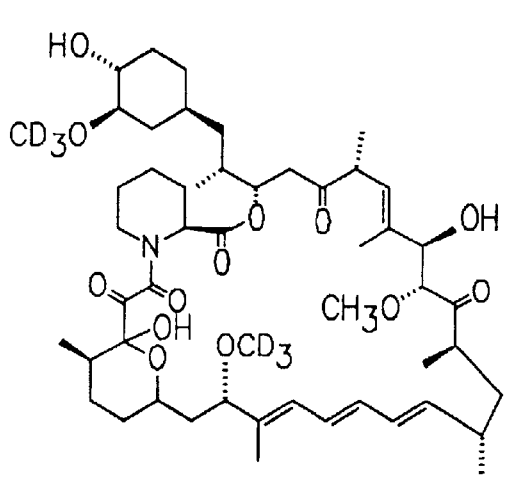
FIG. 3 is the chemical structure of 7,43-$d_6$-rapamycin showing sites of deuteration.
Figure 4:
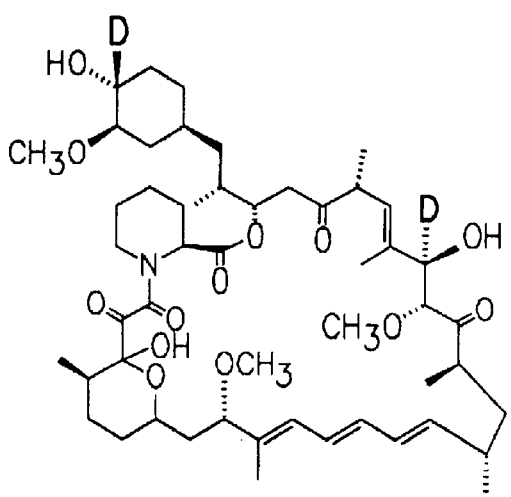
FIG. 4 is the chemical structure of 31,42-$d_2$ showing sites of deuteration.

Preparation of 31, 42 $d_2$-7-deuterated Rapamycin (FIG. 3)

Rapamycin (11 mM) was dissolved in a mixture of cyclohexane and dichloromethane (1:1) 10 ml. The contents were cooled in ice bath and poly(vinylpyridinium) dichromate 0.5 grams was added. The reaction mixture was stirred overnight and the reaction was followed by mass spectrum. The reaction mixture was filtered, washed with water and dried using anhydrous magnesium sulphate. The organic solution was filtered and concentrated. The crude product was subjected to purification by silica column using chloroform-methanol (20:10) mixture. The pure fractions were collected and concentrated. The residue was dissolved in benzene and freeze dried. The product was characterized by LC/MS. M+(Na) 932. This material was dissolved in dry ether (10 ml). 10 equivalents of lithium aluminum deuteride was added. The reaction mixture was stirred for 24 hours. After the completion of the reaction, the excess of $LiAlD_4$ was decomposed by the addition of acetone. The complex was decomposed by adding ice cooled acetic-acid. The mixture is filtered. The filtrate was diluted with ether and washed with water, dried, and concentrated. The crude mixture was subjected to column chromatography and the required material was eluted using chloroform-methanol solvent system. The pure fractions were collected and concentrated. The compound was tested by mass spectrum.

M=(Na) 940. This compound was converted to the desired final compound (2) by following the procedure as described in Example 1.

Example 3

Preparation of Glycosylated deuteroRapamycin (FIG. 5)

Referring to FIG. 5, compound 10 prepared by example 1 (20 mg) was dissolved in 5 ml of dichloromethane. Dimethylaminopyridine (2.2 mg) was added to the above solution. The contents were cooled to −70 C. 4-Nitrophenylchloroformate in dichloromethane was added to the reaction mixture. The solution was stirred under nitrogen at room temperature for 14 hours. The reaction was followed by mass spectrum. After the completion of the reaction, the reaction mixture was diluted with dichloromethane and the organic solution was washed with water, 0.2M ice cold HCl solution. The organic layer was dried over anhydrous magnesium sulphate. After filtration, the organic solution was filtered and concentrated. The crude product was purified by LC/MS to provide the pure compound 30 (Yield 10 mg.) Compound 30 (0.9 m.mol)was dissolved in dry DMF(0.5 ml) To this mixture, a solution of 2-aminoethyl-a-D-glucopyranoside (7.2 m.mol) was added. The reaction mixture was stirred for 14 hours at room temperature. After the completion of the reaction, the mixture was diluted with dichloromethane. The organic solution was concentrated in vacuum. The residue was extracted with water and the aqueous solution was subjected to biogel column to get the required pure compound 50. This material was characterized by LC/MS. M+(Na)1185.

Further variations and modifications of the present invention will be apparent to those skilled in the art from the foregoing and are intended to be encompassed by the claims appended hereto.

We claim:

1. A deuterated rapamycin compound that is selected from the group consisting of 7-deuteromethyl rapamycin and 31,42-$d_2$-rapamycin and isomers thereof.

2. The deuterated rapamycin compound of claim 1 wherein the rapamycin compound is 7-deuteromethyl rapamycin.

3. The deuterated rapamycin compound of claim 1 wherein the rapamycin compound is 31,42-$d_2$-rapamycin.

4. The deuterated rapamycin compound of claim 1 wherein the deuterated rapamycin compound is glycosylated at position 42.

5. The deuterated rapamycin compound of claim 2 wherein the deuterated rapamycin compound is glycosylated at position 42.

6. The deuterated rapamycin compound of claim 3 wherein the deuterated rapamycin compound is glycosylated at position 42.

7. The deuterated rapamycin compound of claim 4 wherein the glycosylated deuterorapamycin has the structure:

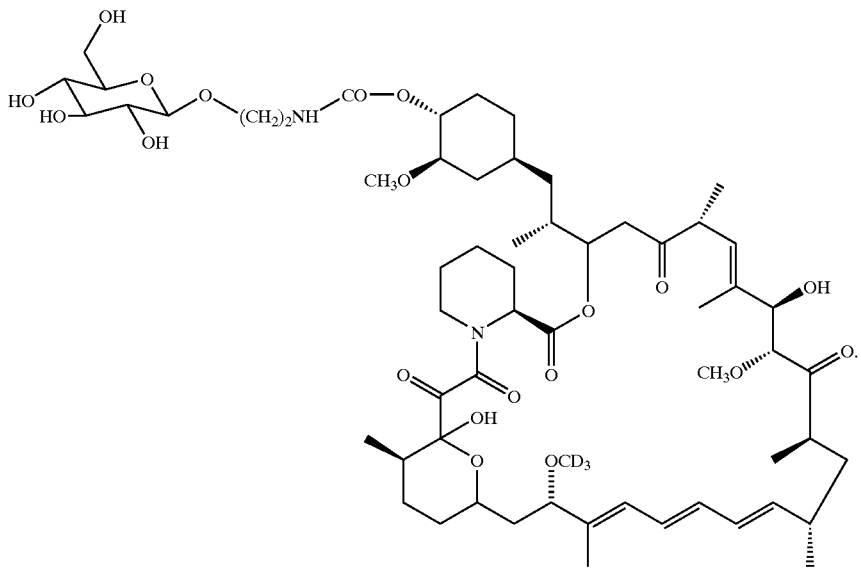

8. A pharmaceutical composition comprising deuterated rapamycin or a pharmaceutically acceptable salt thereof and a pharmaceutically acceptable carrier, wherein the deuterated rapamycin is selected from the group consisting of 7-deuteromethyl rapamycin and 31,42-$d_2$-rapamycin and isomers thereof.

9. The pharmaceutical composition of claim 8 that is in tablet form.

10. The pharmaceutical composition of claim 8 wherein the deuterated rapamycin or a pharmaceutically acceptable salt thereof is 7-deuteromethyl rapamycin.

11. The pharmaceutical composition of claim 8 wherein the deuterated rapamycin or a pharmaceutically acceptable salt thereof is 31,42-$d_2$-rapamycin.

12. The pharmaceutical composition of claim 8 wherein the deuterated rapamycin or a pharmaceutically acceptable salt thereof is glycosylated at position 42.

13. The pharmaceutical composition of claim 10 wherein the deuterated rapamycin or a pharmaceutically acceptable salt thereof is glycosylated at position 42.

14. The pharmaceutical composition of claim 11 wherein the deuterated rapamycin or a pharmaceutically acceptable salt thereof is glycosylated at position 42.

15. The pharmaceutical composition of claim 12 wherein the glycosylated deuterated rapamycin has the structure:

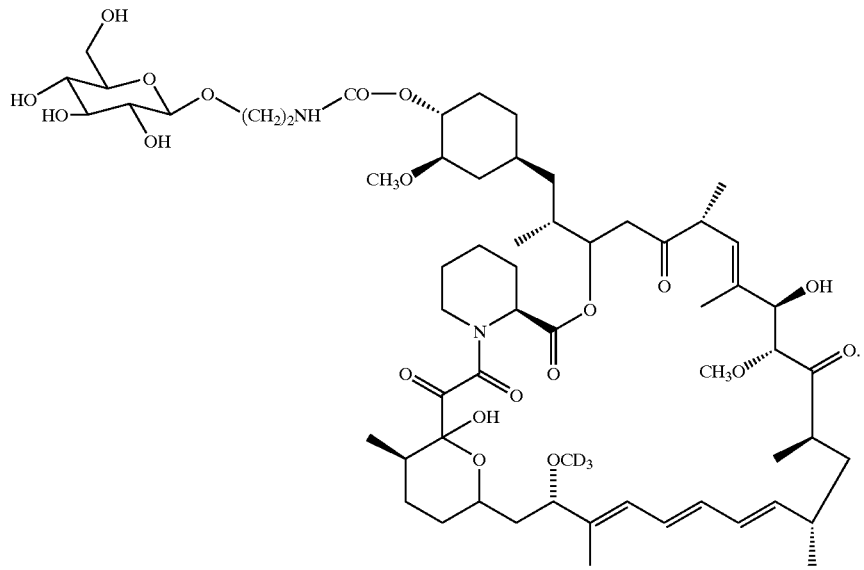

16. The deuterated rapamycin compound which is epi-7-deuteromethyl rapamycin and which is glycosylated at position 42.

17. The deuterated rapamycin compound which is 7,43-$d_6$-rapamycin and which is glycosylated at position 42.

18. A pharmaceutical composition comprising deuterated rapamycin or a pharmaceutically acceptable salt thereof and a pharmaceutically acceptable carrier, wherein the deuterated rapamycin is epi-7-deuteromethyl rapamycin and which is glycosylated at position 42 and isomers thereof.

19. The pharmaceutical composition of claim 18 that is in tablet form.

20. A pharmaceutical composition comprising deuterated rapamycin or a pharmaceutically acceptable salt thereof and a pharmaceutically acceptable carrier, wherein the deuterated rapamycin is 7,43-$d_6$-rapamycin and which is glycosylated at position 42 and isomers thereof.

21. The pharmaceutical composition of claim 20 that is in tablet form.

* * * * *